(12) United States Patent
Bowen

(10) Patent No.: US 6,190,168 B1
(45) Date of Patent: Feb. 20, 2001

(54) DENTAL HANDPIECE HAVING IMPROVED BUR RELEASE MEANS

(76) Inventor: Stanley A. Bowen, 19201 La Loma Dr., Santa Ana, CA (US) 92705

( * ) Notice: Under 35 U.S.C. 154(b), the term of this patent shall be extended for 0 days.

(21) Appl. No.: 09/251,160

(22) Filed: Feb. 17, 1999

(51) Int. Cl.[7] .................................................. A61C 1/14
(52) U.S. Cl. ............................................................ 433/127
(58) Field of Search .............................................. 433/127

(56) References Cited

U.S. PATENT DOCUMENTS

| | | | |
|---|---|---|---|
| 4,874,314 | * 10/1989 | Fleer et al. | 433/127 |
| 5,040,980 | * 8/1991 | Heil | 433/127 |

* cited by examiner

Primary Examiner—John J. Wilson
(74) Attorney, Agent, or Firm—Morland C. Fischer

(57) ABSTRACT

A dental handpiece to releasably retain a workpiece (e.g. a dental bur) that is used to treat the teeth of a patient. The workpiece is clamped within a hollow collet between a pair of flexible clamping fingers having a spring-like memory. A collet actuator is arranged in spaced axial alignment with the collet. Both the collet and collet actuator are surrounded by a cylindrical spindle. An axial pushing force applied to a push-button of the handpiece causes the collet actuator to slide through the spindle towards the collet. A pair of wedge-shaped tips having an angle of approximately 22 degrees are carried by the collet actuator into the hollow collet to stress the pair of flexible clamping fingers thereof. Accordingly, the clamping fingers are rotated outwardly and away from one another through a stroke gap so as to be moved into contact with the spindle, whereby the workpiece is released for removal from the collet.

9 Claims, 3 Drawing Sheets

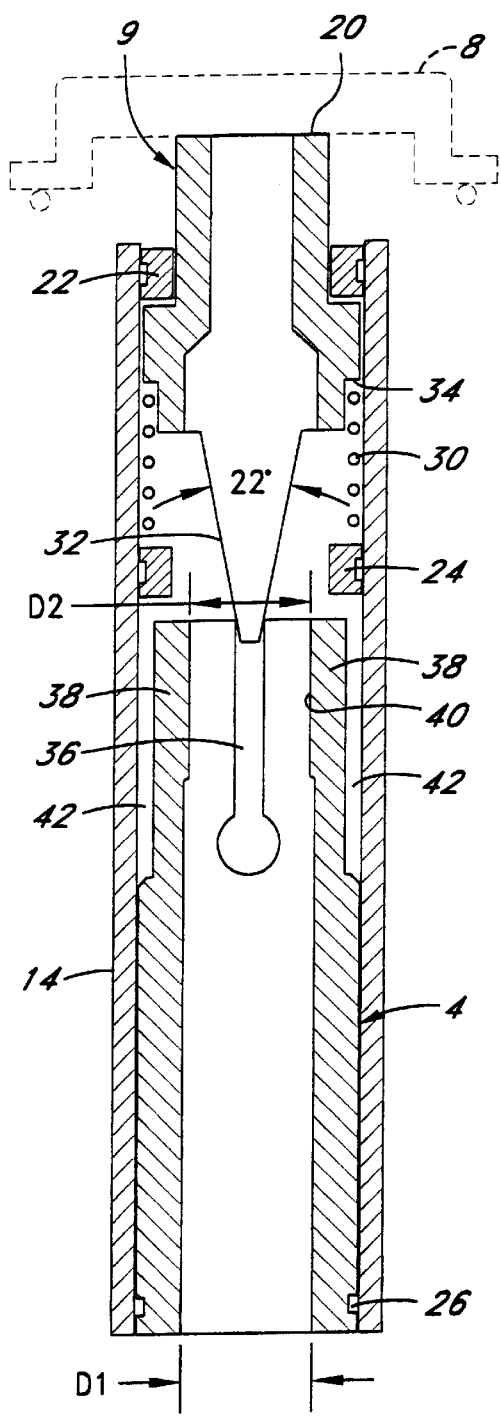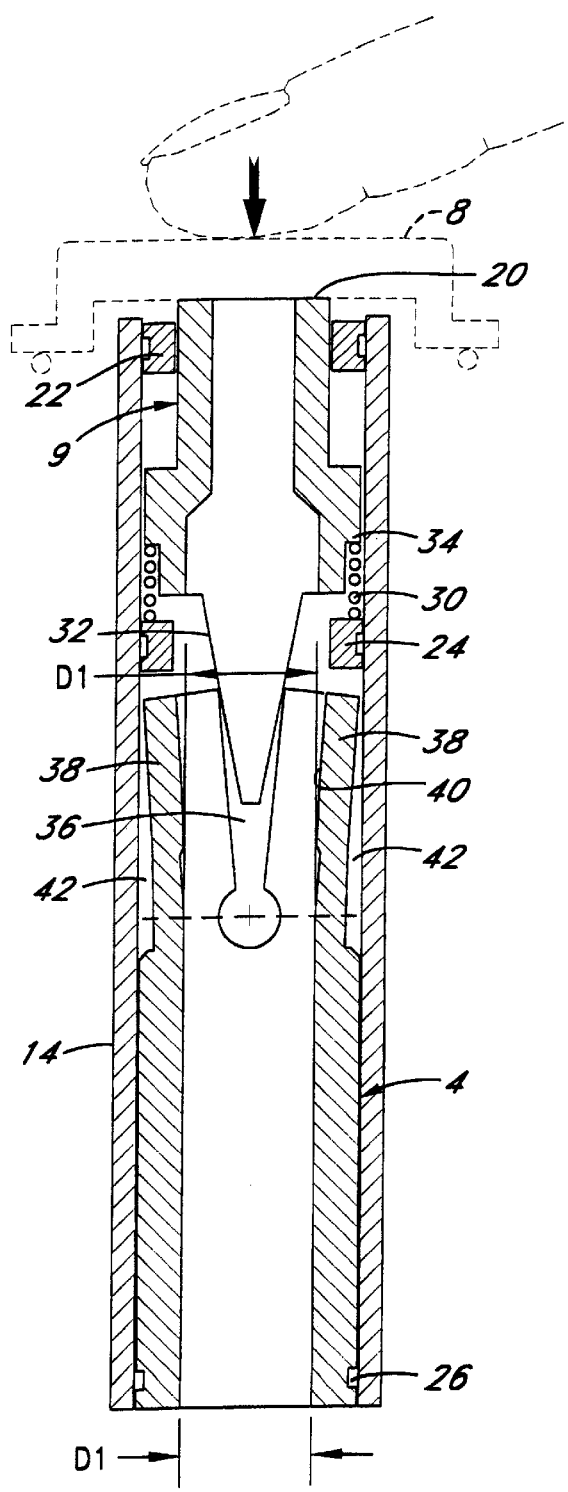
*Fig. 2*  *Fig. 3*

DENTAL HANDPIECE HAVING IMPROVED BUR RELEASE MEANS

BACKGROUND OF THE INVENTION

1. Field of the Invention

This invention relates to a dental handpiece for retaining a conventional dental bur or similar workpiece and to an improved release means by which the bur can be easily removed from the handpiece while minimizing the manual pushing force that is necessary to actuate the release means.

2. Background Art

Compressed air driven dental handpieces have long been used by dental workers to treat the teeth of their patients. One of a variety of workpieces (e.g. a dental bur) is releasably connected to a hollow cylindrical collet of the handpiece so as to be rotatable in response to a corresponding rotational force that is applied to the collet.

From time-to-time, it is necessary to remove the dental bur from the handpiece for purposes of repair, cleaning or replacement by a different workpiece. To accomplish the foregoing, the dental worker typically exerts a pushing force against a push-button of the handpiece which is ultimately transmitted to the collet so as to cause the collet to release its grip on the bur. However, it has been found that a large pushing force is often required before the bur will be released by the collet. Such a large pushing force has heretofor been necessary because of the shape of a collet actuator of the handpiece that transmits the pushing force from the push-button to the collet. More particularly, one well known collet actuator has a pair of wedge-shaped tips that form relatively large angles of about 30 degrees. The collet actuator is moved axially by the push-button so that the wedge shaped tips thereof are received by the hollow cylindrical collet to cause flexible clamping fingers of a collet to rotate outwardly and thereby release their grip upon the bur.

As a consequence of the large angle of the wedge-shaped tips of the collet actuator and the large pushing force that is transmitted to the collet, the flexible clamping fingers of the collet have been known to rotate through a correspondingly large arc. On occasion, this large rotation has significantly reduced the spring-like memory of the flexible clamping fingers of the collet. In this case, the collet may become deformed which undesirably effects its ability to reliably retain a dental workpiece between the flexible clamping fingers. Accordingly, it may be necessary to repair the dental handpiece and/or replace the collet which increases both the cost and downtime to the dental worker.

What is needed is a dental handpiece having an improved workpiece (e.g. bur) release means that reduces the manual pushing force required to release the workpiece as well as the likelihood that the collet will be deformed as the workpiece is released.

SUMMARY OF THE INVENTION

In general terms, a compressed air driven dental handpiece is disclosed having improved bur (or other dental workpiece) release means. The bur is releasably secured between a pair of opposing clamping fingers that are separated from one another by a pair of slots formed through the proximal end of a hollow cylindrical collet. The clamping fingers are characterized by a spring-like memory and the ability to rotate outwardly and away from one another to release their grip on the bur. A collet actuator is held by a compression spring in spaced axial alignment with the collet. The actuator has a pair of wedge-shaped tips that are aligned for receipt by respective ones of a pair of slots at the proximal end of the collet. As an important detail of this invention, each of the wedge-shaped tips forms a relatively narrow angle of about 22 degrees. Both the collet and the collet actuator are surrounded by a cylindrical spindle. The collet is staked to the interior of the spindle, while the collet actuator is adapted to slide reciprocally through the spindle relative to the collet.

In operation, the dental worker applies an axial pushing force to a push-button of the handpiece. The pushing force is transferred from the push-button to the collet actuator, whereupon the actuator is caused to slide through the spindle and towards the collet. Accordingly, the pair of wedge-shaped tips of the actuator move through the respective slots at the proximal end of the collet in order to stress the flexible clamping fingers of the collet and cause the compression spring to be compressed and store energy. The flexible fingers of the collet are now rotated outwardly and away from one another so as to be displaced through a stroke gap of about 0.004 inches to strike the cylindrical spindle. At this point, the dental bur may be easily removed from the distal end of the collet.

By virtue of the narrow angle of the wedge-shaped tips of the collet actuator, the pushing force initially applied to the push-button to move the tips through the slots of the collet to stress the flexible clamping fingers thereof is reduced. What is more, by rotating the flexible clamping fingers of the collet into contact with the spindle, the arc through which the fingers rotate is controlled (i.e. limited) so as to prevent the possible loss of the spring-like memory of the flexible fingers and a deformation of the collet.

When the pushing force applied to the push-button is removed, the compression spring will expand and release energy. The collet actuator is then driven through the spindle away from the collet, such that the wedge-shaped tips of the actuator are withdrawn from the slots at the proximal end of the collet. The spring-like memory of the flexible clamping fingers now causes the fingers to automatically rotate inwardly and towards one another so as to move back to their initial unstressed position at which to clamp the same or a different workpiece therebetween.

BRIEF DESCRIPTION OF THE DRAWINGS

FIG. 2 is an enlarged detail of the bur release means of the dental handpiece of FIG. 1 in the at-rest condition;

FIG. 3 shows the bur release means of FIG. 2 with an axial pushing force applied to cause the release of a dental bur.

DETAILED DESCRIPTION

Figure 1:
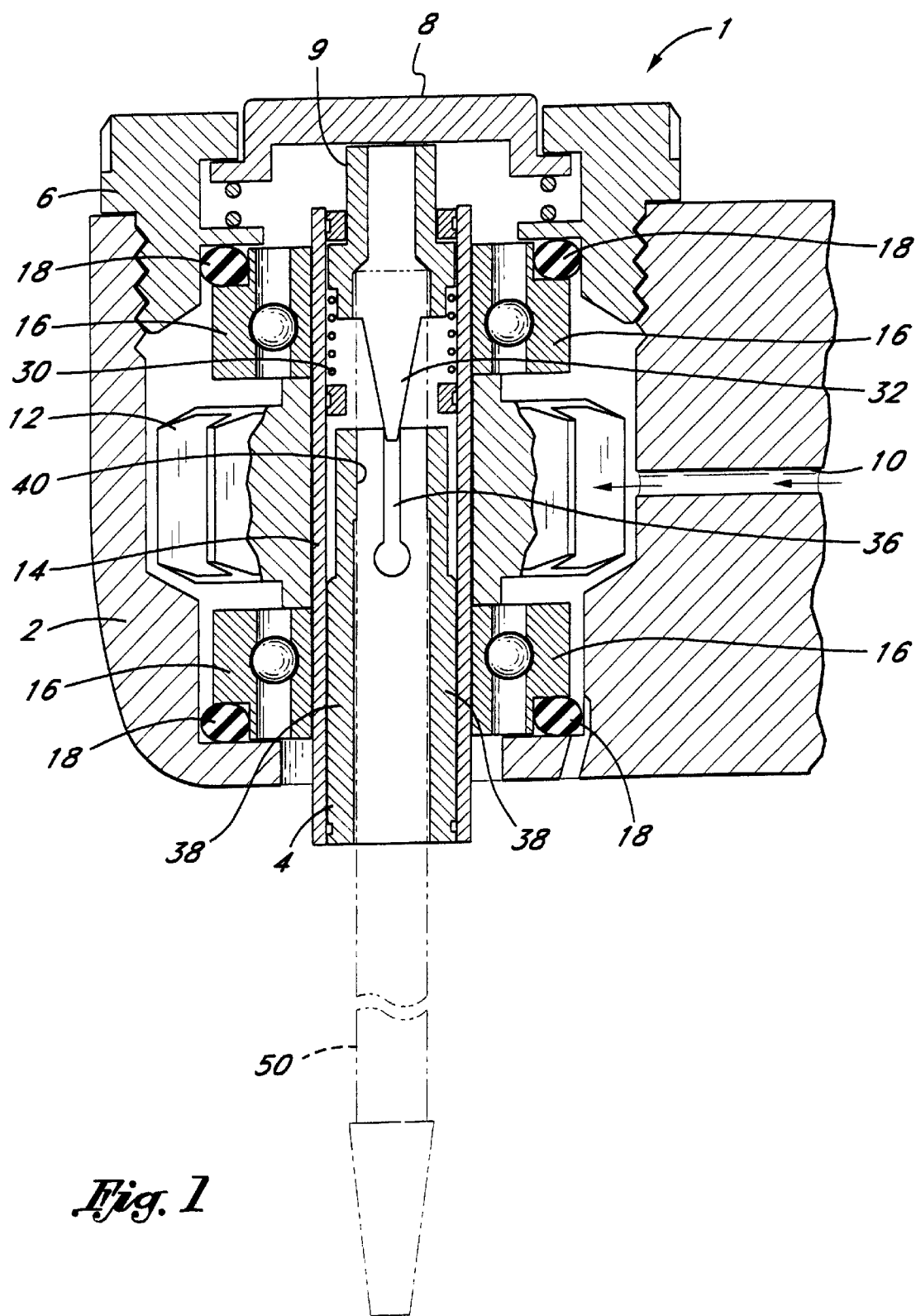
FIG. 1 is a cross-section showing the housing at the head of a dental handpiece having the improved bur release means which forms the present invention.

The dental handpiece and the dental bur release means thereof which form the present invention are now described in detail while referring to the drawings. FIG. 1 shows the housing 2 at the head of a dental handpiece 1 which encloses a steel collet 4 to which a conventional dental bur is detachably connected. A threaded end cap 6 is mated to a threaded portion of the housing 2. End cap 6 supports a spring biased push-button 8. The end cap 6 engages an actuator 9 which is held in spaced axial alignment with collet 4. As will be explained in greater detail hereinafter when referring to FIGS. 2 and 3, an axial pushing force applied to push-button 8 is transferred to the actuator 9, whereby to cause the actuator 9 to slide through the housing 2 and towards the collet 4 so that the dental bur 50 will be released from the collet.

As is common with most commercially available dental handpieces, the head of handpiece 1 contains an air passage 10 that extends between a source of compressed air (not shown) and an air driver turbine 12. The turbine 12 is arranged in surrounding engagement with the bur retaining collet 4. Compressed air being forced through air passage 10 causes the turbine 12 to rotate, which rotation is transferred to the collet 4 and then to the dental bur 50. To accomplish the foregoing and maintain the axial alignment of the actuator 9 with the collet 4, the collet 4 and actuator 9 are surrounded by a hollow cylindrical spindle 14 that is retained within the housing 2 of handpiece 1. Bearings 16 support the spindle 14 and the collet 4 for rotation in response to a rotation of the air driven turbine 12, whereby to correspondingly cause the dental bur 50 to rotate. Bearings 16 are retained within the housing 2 by means of the usual rubber O-rings 18, or the like.

FIG. 2 of the drawings shows the collet 4 at rest when no pushing force is applied to the actuator 9 via the push-button 8 of the dental handpiece 1 of FIG. 1. Actuator 9 has a relatively narrow force receiving end 20 that communicates with push-button 8 so that actuator 9 is adapted to slide in reciprocal directions through the spindle 14 relative to the collet 4 depending upon whether push-button 8 has been depressed by a dental worker.

A first retaining ring 22 surrounds the force receiving end 20 of actuator 9 at one end of the hollow cylindrical spindle 14 to prevent the actuator from being pulled out of the spindle. A second retaining ring 24 is disposed within spindle 14 and spaced axially from the first retaining ring 22. Each of the retaining rings 22 and 24 is staked in place within the spindle 14. However, for ease in assembly, the spindle 14 may be manufactured with retaining ring 24 as an integral part thereof Another stake 26 fixes the position of the collet 4 within spindle 14 so that the collet cannot be displaced relative to the spindle.

A closed end, coiled compression spring 30 that is typically manufactured from spring steel is located within the cylindrical spindle 14 to control the axial (i.e. reciprocal) movement of actuator 9 through spindle 14 in a manner that will be described when referring to FIG. 3. Compression spring 30 surrounds a pair of wedge shaped tips 32 that project from the actuator 9 (best shown in FIG. 4). Compression spring 30 extends between the second retaining ring 24 within spindle 14 and a spring retaining notch 34 that is formed in the actuator 9. As an important improvement of this invention, each of the wedge shaped tips 32 of actuator 9 form an angle that lies in a range of angles between 18 to 24 degrees, as opposed to a 30 degree angle that has heretofor been characteristic of some conventional actuators. In the preferred embodiment, the wedge shaped tips 32 form an angle of 22 degrees, as illustrated.

In the at-rest condition of the actuator 9 (with no pushing force applied to the force receiving end 20 thereof), the compression spring 30 will be in a relaxed, expanded condition as shown in FIG. 2. In this regard, the compression spring 30 maintains the actuator 9 in spaced axial alignment with the collet 4 at the interior of cylindrical spindle 14, such that the pair of wedge shaped tips 32 of the actuator are received at the entrance to a respective pair of slots 36 that run axially through actuator 9 from the proximal end thereof It is important to note that the wedge shaped tips 32 of actuator 9 are wider than the slots 36 of collet 4 at which tips 32 are received. The axially running slots 36 establish a pair of opposing, semi-cylindrical clamping fingers 38 at the proximal end of the collet 4 (also best shown in FIG. 4). The clamping fingers 38 are characterized by a spring-like memory and the ability to flex or rotate under stress. Moreover, the clamping fingers 38 have a reduced diameter area 40, the inside diameter of which (designated D2 in FIG. 2) is less than the inside diameter (designated D1) of the cylindrical spindle 14. That is to say, by virtue of the reduced diameter area 40 of the flexible fingers 36 of collet 4, the dental bur (designated 50 in FIG. 1) is reliably clamped within the collet. A stroke gap 42 of approximately 0.004 inches is formed between the clamping fingers 38 and the cylindrical spindle 14 that surrounds the collet 4 and actuator 9.

Turning now to FIG. 3 of the drawings, an axial pushing force is applied to the force receiving end 20 of the actuator 9 when a dental worker depresses the push-button 8 of the handpiece 1. This axial pushing force at force receiving end 20 causes the actuator 9 to slide through the cylindrical spindle 14 in a direction towards the collet 4. As actuator 9 slides towards collet 4, the compression spring 30 is correspondingly compressed between the spring retaining notch 34 of actuator 9 and the retaining ring 24, the position of which is fixed within the spindle 14. At this point, compression spring 30 stores potential energy.

Accordingly, the pair of wedge shaped tips 32 of actuator 9 are pushed into the pair of axial slots 36 of the collet 4. As was previously disclosed, the wedge shaped tips 32 form a relatively small angle (of preferably 22 degrees). This angle and the fact that the wedge shaped tips 32 are wider than the width of axial slots 36 cause the flexible clamping fingers 38 at the proximal end of collet 4 to rotate outwardly and away from one another towards spindle 14 as the tips 32 are forced through respective slots 36 so as to cause collet 4 to release its grip on the dental bur.

More particularly, it has been found that the improved angle of the wedge shaped tips 32 of actuator 9 sufficiently stresses the flexible fingers 38 of collet 4 so that fingers 38 rotate completely through the stroke gap 42 to strike spindle 14 while minimizing the axial pushing force necessary to move the wedge shaped tips 32 through slots 36. The dental worker can now simply remove (and replace) the existing dental bur from the distal end of the collet 4, inasmuch as the bur is no longer clamped at the reduced diameter area 40 of the flexible fingers 38. At the same time, striking the spindle 14 limits the rotation of the flexible fingers 38 so as to avoid a deformation of the collet 4 and a possible loss of the spring-like memory in fingers 38.

When the axial pushing force is removed from the force receiving end 20 of the actuator 9, the potential energy stored by compression spring 30 is released. The spring 30 will begin to expand and thereby drive the actuator 9 axially through spindle 14 in an opposite direction away from the collet 4. Accordingly, the wedge shaped tips 32 of actuator 9 are pulled outwardly from the axially running slots 36 of the collet 4, whereby the spring-like memory of the flexible fingers 38 at the proximal end of the collet causes the fingers to rotate inwardly towards one another through the stroke gap 42 and back to their initial, unstressed position as shown in FIG. 2. However, any new dental bur (or other workpiece) which is inserted within the distal end of collet 4 will be connected to the dental handpiece 1 and clamped between the reduced diameter area 40 of the clamping fingers 38.

Figure 4:
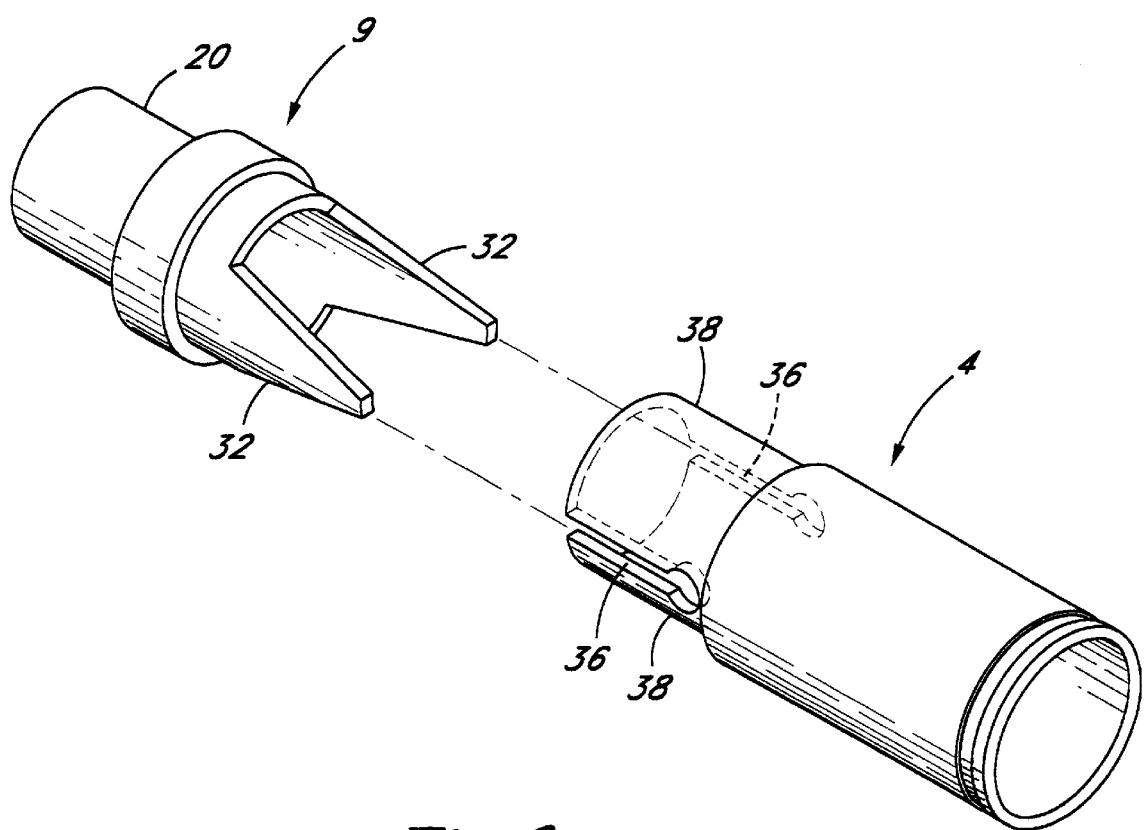
FIG. 4 is an exploded perspective view to illustrate the spaced axial alignment of a collet and a collet actuator which form the bur release means of this invention.

FIG. 4 of the drawings shows the spaced axial alignment of the actuator 9 with the collet 4 of the dental handpiece 1 of FIG. 1. FIG. 4 also shows the wedge shaped tips 32 projecting from the actuator 9 and adapted to be moved towards and into receipt by the respective axially running slots 36 that separate the flexible clamping fingers 38 at the proximal end of collet 4 when an axial pushing force is applied to the force receiving end 20 of actuator 9 in the manner that was previously disclosed when referring to FIG. 3 so that a dental bur can be removed from (or inserted within) the distal end of the collet.

I claim:

1. A dental handpiece for holding a workpiece that is used to treat the teeth of a patient, said dental handpiece including:
   - a hollow collet having proximal and distal ends, the workpiece being removably received through said distal end so as to be surrounded by said collet and clamped at said proximal end thereof;
   - a collet actuator disposed in spaced axial alignment with said collet, said collet actuator having workpiece release means sized so as to be received inwardly through the proximal end of said collet;
   - a cylindrical spindle surrounding each of said axially aligned collet and collet actuator, said collet being fixedly attached to said spindle and said collet actuator being slidable reciprocally through said spindle relative to said collet;
   - a push-button to which an axial pushing force is applied, said axial pushing force being transferred from said push button to said collet actuator to cause said collet actuator to slide through said spindle towards said collet so that said workpiece release means of said collet actuator is pushed into the proximal end of said collet to force said proximal end to move outwardly and into contact with said spindle, whereby to release the workpiece from said collet; and
   - spring means aligned for engagement by said collet actuator, said spring means being compressed by said collet actuator when said collet actuator is pushed through said spindle and moved towards said collet in response to the axial pushing force applied to said push-button, and said spring means expanding to cause said collet actuator to slide through said spindle and away from said collet when said axial pushing force is terminated.

2. The dental handpiece recited in claim 1, wherein the workpiece release means of said collet actuator has a wedge shape that forms an angle lying in a range of angles between 18 to 24 degrees.

3. The dental handpiece recited in claim 2, wherein the angle formed by said wedge-shaped workpiece release means of said collet actuator is 22 degrees.

4. The dental handpiece recited in claim 1, wherein each of the proximal and distal ends of said hollow collet has an inside diameter, the inside diameter of said proximal end at which the workpiece is clamped being less than the inside diameter of said distal end.

5. The dental handpiece recited in claim 1, wherein the proximal end of said hollow collet at which the workpiece is clamped comprises a plurality of flexible fingers having a spring memory, said plurality of flexible fingers adapted to rotate outwardly and away from one another so as to move into contact with said spindle in response to the workpiece release means of said collet actuator being pushed into the proximal end of said collet.

6. The dental handpiece recited in claim 5, wherein the workpiece release means of said collet actuator includes a plurality of wedge shaped tips that are pushed into the proximal end of said hollow collet to force respective ones of said plurality of flexible fingers of said collet to rotate outwardly and away from one another so as to move into contact with said spindle to release the workpiece from said collet.

7. The dental handpiece recited in claim 6, wherein each of the plurality of wedge shaped tips of said collet actuator forms an angle of approximately 22 degrees.

8. The dental handpiece recited in claim 6, wherein each of the proximal and distal ends of said hollow collet has an outside diameter, the outside diameter of said proximal end being less than the outside diameter of said distal end such that a stroke gap is established between said proximal end and said spindle, said plurality of flexible fingers at the proximal end of said collet rotating through said stroke gap so as to move into contact with said spindle when the plurality of wedge shaped tips of said collet actuator are pushed into the proximal end of said collet.

9. The dental handpiece recited in claim 1, wherein said spring means is a coiled compression spring that surrounds at least some of said collet actuator, said collet actuator having a notch formed therein at which to engage said coiled compression spring.

* * * * *